US009445078B2

(12) United States Patent
Sneyders et al.

(10) Patent No.: US 9,445,078 B2
(45) Date of Patent: Sep. 13, 2016

(54) STEREO-VISION SYSTEM

(75) Inventors: Emmanuel Sneyders, Turnhout (BE);
Jean Marie Stassen, Heverlee (BE);
Hans Nicasy, Turnhout (BE)

(73) Assignees: ThromboGenics NV, Deurne (BE);
Peira BVBA, Deurne (BE)

(*) Notice: Subject to any disclaimer, the term of this patent is extended or adjusted under 35 U.S.C. 154(b) by 339 days.

(21) Appl. No.: 14/114,569

(22) PCT Filed: Apr. 27, 2012

(86) PCT No.: PCT/EP2012/057776
§ 371 (c)(1),
(2), (4) Date: Oct. 29, 2013

(87) PCT Pub. No.: WO2012/146720
PCT Pub. Date: Nov. 1, 2012

(65) Prior Publication Data
US 2014/0111621 A1  Apr. 24, 2014

(30) Foreign Application Priority Data
Apr. 29, 2011  (GB) .................................. 1107225.3

(51) Int. Cl.
*G01B 11/00* (2006.01)
*H04N 13/02* (2006.01)
*G01B 11/25* (2006.01)
*A61B 5/00* (2006.01)
*A61B 5/107* (2006.01)

(52) U.S. Cl.
CPC ......... *H04N 13/0207* (2013.01); *A61B 5/0073* (2013.01); *A61B 5/1079* (2013.01); *G01B 11/2545* (2013.01); *A61B 5/0095* (2013.01); *A61B 2503/42* (2013.01)

(58) Field of Classification Search
CPC .................................................. G01B 11/2545
USPC .......................................................... 348/46
See application file for complete search history.

(56) References Cited

U.S. PATENT DOCUMENTS

| 4,805,638 A | 2/1989 | Steinhauer et al. |
| 2007/0229850 A1 | 10/2007 | Herber |
| 2009/0245603 A1 | 10/2009 | Koruga et al. |

(Continued)

FOREIGN PATENT DOCUMENTS

| CA | 2686904 A1 | 6/2011 |
| WO | 2004048970 A1 | 6/2004 |
| WO | 2007129047 A1 | 11/2007 |

OTHER PUBLICATIONS

Konolige, "Projected Texture Stereo", IEEE, pp. 148-155, May 3, 2010.
Search Report for Application PCT/EP2012/057776 dated Aug. 10, 2012.

(Continued)

*Primary Examiner* — Jeffery Williams
(74) *Attorney, Agent, or Firm* — Dinsmore & Shohl LLP

(57) ABSTRACT

This invention concerns a measuring system for the calculation of dimensions, including area and volume, of objects in various shapes. In particular, it concerns miniature 3D measuring equipment that is perfectly suitable for 3D measurements of subcutaneous tumors in mice. The primary objective of this invention then also consists of a measuring system for 3D measurements of objects in various shapes, which includes a handheld device that has at least 1 camera, 1 projector and a measuring chamber. In another implementation, the handheld device will have 2 cameras and a projector and the 3D measurement is based on stereo-vision. Another objective is directed to ensuring that said handheld device also has a processor module, a user interface, a power supply, a data communication interface, and exchangeable measuring chambers which provide the flexibility and autonomy to speed up the measurement procedure, and significantly improve the reproducibility of the measurement.

20 Claims, 2 Drawing Sheets

(56) References Cited

U.S. PATENT DOCUMENTS

2010/0201784 A1 8/2010 Lippert et al.
2011/0080471 A1* 4/2011 Song ................... G01B 11/245
　　　　　　　　　　　　　　　　　　348/46

OTHER PUBLICATIONS

International Preliminary Report on Patentability for Application PCT/EP2012/057776 dated Jul. 26, 2013.

* cited by examiner

STEREO-VISION SYSTEM

DOMAIN OF THE INVENTION

This invention concerns a measuring system for the calculation of dimensions, including surface and volume, of objects in various shapes. In particular, it concerns miniature 3D measuring equipment that is perfectly suitable for 3D measurements of subcutaneous tumours in mice. The primary objective of this invention then also consists of a measuring system for 3D measurements of objects in various shapes, which includes a handheld device that has at least 1 image capturing device, hereinafter also referred to as sensor, at least one measuring source, in particular a projector and a measuring chamber. In a more specific implementation, the handheld device will have 1 or 2, in particular 2 cameras and a projector and the 3D measurement is based on stereo-vision.

It is also the objective of the current invention of a measurement system to ensure that said handheld device also has a processor module, a user interface, power supply and a data communication interface, and exchangeable measuring chambers to give the device the necessary flexibility and autonomy to speed up the measurement procedure, and to significantly improve the reproducibility of the measurement.

POSITIONING OF THE INVENTION

After the functional identification of a new target for combating cancer, various products focus on the target selected based on their selectivity for the target. Next, the activity, the efficacy and the safety- and toxicity profile of the candidate medicines must be compared in an extensive screening process. This screening process is performed in preclinical animal models before the clinical trials on the product may start. The time required for animal experiments is often a principle issue in the development of potential medicines for cancer due to the absence of high-throughput screening models.

The tumour size is the primary focus in most preclinical activity studies. Efficacy and accurate measurements of the tumours are thus crucial for a speedy evaluation of new candidate medicines. An important part of these in vivo studies occur in mice, whereby the effect of the test components on subcutaneous or orthotopic tumours is studied. The subcutaneous tumour models with immune deficiency, naked mice are used most frequently. In this model, the tumour growth is clearly visible through the skin that enables a simple, non-invasive monitoring of the growth.

There are already numerous advanced commercial and experimental techniques such as 'Computed Tomography (CT)', 'Magnetic Resonance Imaging (MRI)' and 'Tomographic Fluorescence (FMT)' available for macroscopic imaging. However, these oncological research methods are very costly, and the usability in the current environment and the availability are major limiting factors for use in long-term experiments, where the tumour growth is monitored frequently. It is often also not easy to standardise these methods or to perform it quickly. These techniques can thus not be used as high-throughput screening systems. Further, there are also optical systems based on a so-called line scanner that can be used effectively to measure tumours in mice, for example the system of Biopticon (A structured light-based system for scanning subcutaneous tumours in laboratory animals, such as for example described in U.S. Pat. No. 7,450,783). However, these systems are relatively expensive and large as the line projector is based on a laser. In addition to this, a full scan of the surface to be measured lasts a few seconds during which the mouse must be perfectly stabilised.

For this reason, the subcutaneous tumour growth is often measured with a caliper, which enables simple and fast measurements (see FIG. 1A). The tumour size is then calculated according to the 2 dimensional horizontal diameters and the maximum height. As the tumours grow, the shapes can strongly deviate from the theoretic semi ellipsoidal shape (see FIG. 1B). The calculated shape is thus only an estimate that could strongly deviate from the actual tumour size. Not only intensive training and experience are required for reproducible measurements, more animals are also needed for effective results.

With this application, the applicant then also provides the realization of highly technological 3D measurement equipment that enables accurate, easy and quick measurement of the growth of subcutaneous tumours. With the new measuring equipment, the preclinical screening process is accelerated in two directions. On the one hand, the measurement is fully automated and on the other hand, the variability of the measurements are minimised, which will increase the efficacy of the preclinical experiments.

Further and different to 3D measurement systems known in the art, the system has been adapted for the measurement of small objects with non-geometric forms using a handheld device and exchangeable measuring chambers according to the dimensions of the objects to be measured. For example when compared to the 3D-photography system described in European patent publication EP140870, the 3D-measuring system of the present invention does not include a projection view angle adjusting unit to enable a single camera making photographs from the same object from different view angles, the latter being combined in a D-stereovision algorithm. It further lacks an exchangeable (removable) measuring chamber fitting over the object to be measured. The same applies for the 3D-measuring apparatus described in U.S. Pat. No. 4,805,638. Said reference provides a device for photogrammetrical measurement of the human head, but as evident from the drawings this system does not include a handheld device with an exchangeable (removable) measuring chamber. Further systems lacking such an exchangeable measuring chamber are for example described in patent references CA2686904, US20070229850, WO2007129047 and US20090245603. CA2686904, WO2007129047 and US20090245603, further differ from the instant device in the measuring method applied. The method in CA2686904 further requires additional light sources and the presence of retro-reflective material next to the object to be measured. This clearly adds further complexity to the measurement and isn't applicable in scanning of subcutaneous tumours in laboratory animals as described hereinbefore. Also in the method described in WO2007129047 additional reference targets with predetermined volumes are added to the measuring area. Again, and similar to the method described in CA2686904, this adds further complexity to the measurement and isn't applicable in scanning of subcutaneous tumours in laboratory animals as described hereinbefore. In US20090245603 two images with different illuminations are taken from the objects. In the instant device only one illumination is used, thus simplifying the procedure and assisting in the ease of manipulation of the device.

It is thus an object of the present invention to provide an accurate 3D measuring system, including a handheld device, simple in use and particularly suitable for measuring small objects with variable, non-geometric shapes; in particular of subcutaneous tumours.

DESCRIPTION OF THE INVENTION

Figure 4:
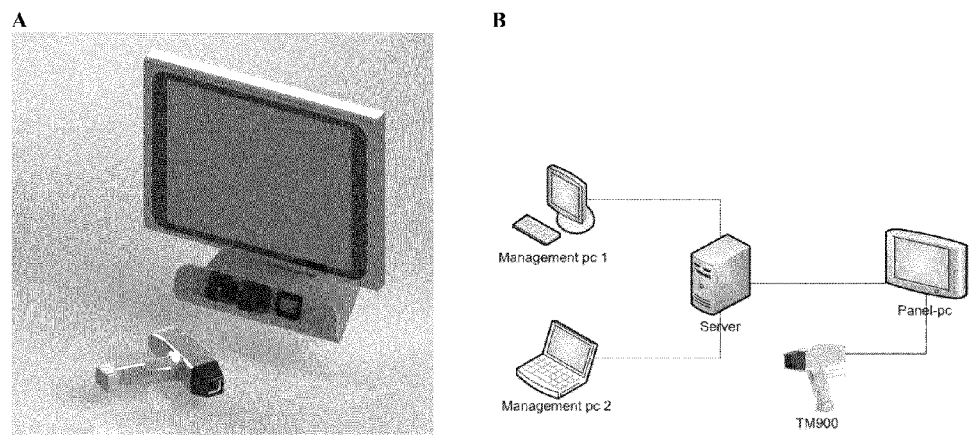
FIG. 4 Base station with panel-pc (A) and block diagram of the architecture of the system (B).

The new monitoring system can automatically perform 4 processes: 1) Projection of a detectable signal using an appropriate measurement source (for example a structured noise pattern using a LED light source, a gobo pattern disk (metal-covered glass disk etched with a pattern) and a condenser) at the surface of the object to be measured, 2) Recording the signal as transformed by the object to be measured using one or more compatible sensors (for example image recording of the structured noise pattern projected on the object to be measured with 1 or 2 digital cameras), 3) Processing of the recorded signal where the data is interpolated to 3D-volume (for example via stereo-vision), 4) Data output. The required hardware and software that automate these processes are included in the set-up that consists of a measuring device and a base station with user interface (for example consisting of a panel-pc (see FIG. 4)), which will enable the operator to perform the measurement accurately. As already indicated above, the new monitoring system is in particular suitable for 3D measurements of subcutaneous tumours in various animal models for cancer. A similar measurement with a caliper, including the data processing generally takes a few minutes. With the new concept, this is reduced to a few seconds. This way, an operator can follow up on 3 times as many experiments in parallel.

The new device does not only speed up the measuring procedure but also reduces the variability of the measurements by an increase of the resolution and accuracy of the measurement. Due to the consistency in the measurements, less animals are required for said cancer models to obtain accurate results (due to reduction of the (intra-) variability between the measures) and the progress of an experiment by another operator can be guaranteed (because the (inter-) variability between the operators are minimised). Since the continuity of the experiments can be guaranteed, the number of studies per year can be increased with 150%.

All these factors ensure that the new measuring device complies with all requirements necessary for a high-throughput screening of the effect of tumour inhibitors on subcutaneous tumour growth. In the current situation, where a caliper is used, an operator can on average follow 2 experiments during a period of 2 months. Annually, approximately 6 experiments are performed per project. With the new monitoring system, the operator will be able to follow 6 experiments in parallel and with the cooperation of multiple operators, an average of 27 experiments can be performed per year per project. Concretely, this means that the development of this unique device speeds up the preclinical screening process of potential cancer medicines with 12 months.

The objectives of this application consist of 3 parts. A first objective is the availability of image recording technology and electronics for 3D measurements of objects with variable, non-geometric shapes, in particular of subcutaneous tumours. The parameters that determine this image recording technology are on the one hand accuracy (spatial resolution) and speed of the measurement and on the other hand, the autonomy and efficiency of the device. In principle any 3D measuring method based on one or more image capturing devices (sensors) and a measurement source can be used, including but not limited to 3D stereovision, hyperspectral imaging, ultrasonography, photoacoustic tomography, thermoacoustic tomography, and the like . . . .

For example, in case of photoacoustic tomography the measurement source will consists of non-ionizing laser pulses delivered to the target. Some of the delivered energy will be absorbed and converted into heat, leading to transient thermoelastic expansion and the generation of ultrasonic waves. Said waves can be detected using one or more ultrasonic transducers (sensors). Since the magnitude of said ultrasonic waves is proportional to the local energy deposition, the former can be to form 3D images of the targeted area. Using photoacoustic tomography high resolution images can be generated of such subcutaneous tumors at depths up to 7 cm. Further depths can be reached by using microwaves or radio frequency (RF) pulses as the excitation source. In said instance the foregoing technology is being referred to as thermoacoustic tomography.

Next, in a second objective of this application, is the availability of a software package with a module for analysis of the recorded signal (for example image analysis in the case of 3D stereovision or ultrasound wave analysis in case of photo- or thermo-acoustic tomography), with image visualisation and data-output. The determining parameters for this software are the speed and autonomy of data processing. Finally, this application has one last objective, to integrate the image recording technology and the software in a set-up (device) compatible with in vivo animal models for cancer (for example mice). This device enables the operator to effectively and accurately measure the size of the subcutaneous tumours in mice. Further, the integration of the device in the research process on "subcutaneous mouse-tumours models" ensures that the "intra-variability" between the measurements of the same tumour by one operator, just like the "inter-variability" between the measurements of the same tumour measured by the various operators, decreases (in comparison to the variability of the current caliper method).

As already indicated above, the new monitoring-, measurement system in one of its objectives is based on aided stereo-vision (Konolige, K., Projected texture stereo, Robotics and Automation (ICRA), 2010 IEEE International Conference on; p. 148-155) for the following reasons;

There are fewer requirements for the projection system. In other concepts, the points are calculated based on the geometrics of the laser projection and the imager. This must be calibrated very carefully and remain stable for a while. With the stereo-vision, it is sufficient for the cameras to be calibrated and that recognisable mark points (for example a structured noise pattern) are created on the volume to be measured.

Since a person wants to take a measurement quickly, the stereo-vision gives the advantage that one image recording (left and right camera image) is enough to take an accurate 3D measurement. Further, one of the camera images (preferably the left one, because this could also be used as reference image) can be stored as historic data.

The cost of the cameras is not a problem for the intended accuracy. 2 cheap cameras, for example as used in SmartPhones, laptops, toys and even gadgets, will suffice. Two such cameras give even more information than 1 expensive camera with expensive lenses.

The abovementioned statement is also applicable to the projector (the measurement source used in this 3D stereovision embodiment of the present invention). A simple, modular, miniature static projector suffices, rather than an expensive laser. The projector technology such as LCD, DLP or CRT, which is currently used in picobeamers, is equally suitable to this invention. The measurement is taken on very short distance, and the difficulty lies in the relatively large depth of field that is required. In a special execution form (embodiment of the present invention), the projector is a compact projector, based on the principle of a slide projector and consisting of a high power LED light source, a gobo pattern disk (metal-covered glass disk etched with a pattern) and a condenser.

Figure 2:
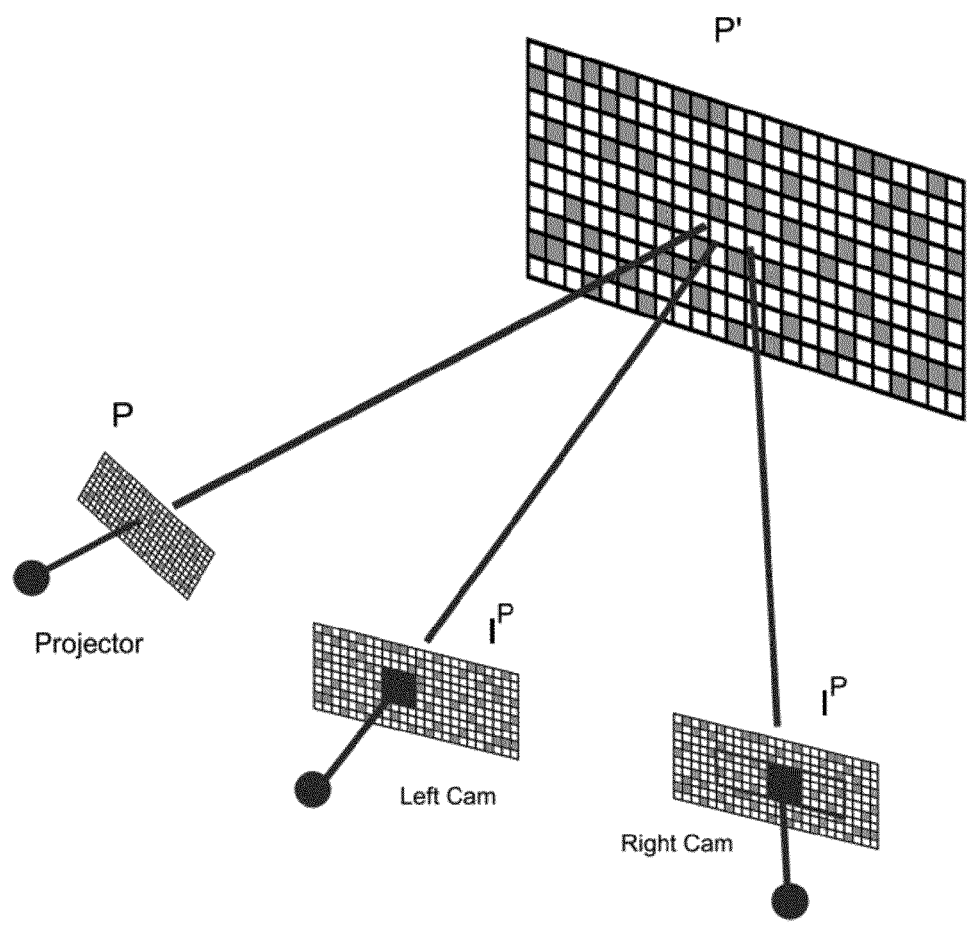
FIG. 2 Schematic diagram of the aided stereo-vision principle.

FIG. 2 illustrates a schematic diagram of the aided stereovision principle. As indicated above, the measuring instrument has two cameras and a projector for this purpose. The latter projects a pattern, preferably a structured noise pattern on the object to be measured.

The system must be calibrated in advance based on actual measurements of known objects (especially a draughts pattern that one can position at various angles and various distances from the camera). This way, the camera parameters such as focus distance, rotation and translation matrix between both cameras and a perspective transformation matrix are retrieved.

For the actual measurement, recognisable measure points (in particular structured noise) are projected on unknown objects via the projector, and which recognisable measure points can be found on both cameras recordings. Via these recognisable measuring points, the corresponding blocks in both images can be retrieved. The shift (in pixels) of such a block between the left and right image can be converted to a point in the 3D area via the earlier determined calibration parameters. This method offers a solid and fast way of measuring.

Execution Form
Product Specifications/Dimensions
Resolution

The development of the measuring system strives for a system that can be broadly used for the calculation of the dimensions, including volume and area, of objects with variable shapes. For this purpose, it is not necessary to be able to observe the finer details of the object and as such, the requirements regarding the resolution does not need to be specified in too much details. In this invention, and in particular in the measurement of subcutaneous tumours in mice, one wants to measure the tumour as quick as possible, where it is most important to have an accurate measurement of the volume and the shape. The accuracy per point thus also ranges from 0.5 to 0.01 mm; in particular approximately 0.3 to 0.1 mm; more specifically, the cameras ideally have a resolution of 0.03 mm per point and a depth resolution of 0.3 mm can be achieved.

Measuring Volume and Measurements (Width, Height, Depth)

As already indicated above, the measuring system of this invention is characterised in comprising a handheld device that has apart from 1 or more sensors (in particular 1 or 2 cameras), at least one measurement source (in particular a projector) and an exchangeable (removable) measurement chamber, to ensure that the objects to be measured are enclosed. There are thus also no specific restrictions concerning the shape or size of this measurement chamber, and in the view of the special application for the measurement of subcutaneous tumours, the typical shapes and dimensions of these tumours will be taken into consideration for determining the dimensions of the interior measures of the measuring chamber. In a first execution form (embodiment), the measurement chamber has a basic length and width of up to approximately 150 mm and a height up to approximately 200 mm; and in particular a length and width of approximately 50 mm and a height of approximately 100 mm; more in particular a length and width of approximately 30 mm and a height of approximately 50 mm; and more specifically a length and width of approximately 22.5 mm and a height of approximately 50 mm; and in its smallest form, a length and width to approximately 15 mm and a height of approximately 50 mm. In the view of the variation in dimensions of the objects to be measured, the measuring chamber will be exchangeable or removable, and according to the dimensions of the objects to be measured, another measuring chamber can be mounted on the handheld device. In this embodiment, the measuring chamber consists of upright faces that fit over the object to be measured on one side and fit on the opposite side on the measuring head of the handheld device, the latter fitted with the 1 or 2 cameras and projector. In a special embodiment, the inside walls of the measurement chamber are laid out in such a way that there are no light reflections, for example via horizontally ribbed panels on one or more internal surfaces of the measurement chamber. In a further embodiment of the present invention, at least one of the upright faces of the exchangeable (removable) measuring chamber allows viewing into the chamber when positioned over the object to be measured. The latter allows better positioning of the measuring chamber over the object to be measured. Any conceivable adaptation to allow the operator of the device to view into the chamber is within the admit of the present invention. In exemplary embodiments at least one of the upright faces of the exchangeable (removable) measuring chamber is either transparent or has been opened.

In an embodiment of the current invention, the handheld device is thus further characterised in the fact that it contains an exchangeable measurement chamber, and the latter has grips for the connection with the measurement head of the handheld device. These could for example consist of a threaded connection, bayonets lock, click confirmation, magnetic fitting, etc. In a special embodiment, the grips consist of a magnetic fitting between the measurement head and the measurement chamber. The exchangeable chambers as used in this invention have dimensions of up to approximately 150 mm at the base and a height of up to approximately 200 mm. In a special embodiment, the measurement chambers has a square basic length and width of up to approximately 150 mm and a height up to approximately 200 mm; and in particular a length and width of approximately up to 50 mm and a height of approximately up to 100 mm; more in particular a length and width of approximately up to 30 mm and a height of approximately up to 50 mm; and more specifically a length and width of approximately 22.5 mm and a height of approximately mm; and in its smallest form, a length and width of approximately 15 mm and a height of approximately 50 mm.

In a further embodiment, the exchangeable measurement chamber has dimension-depending recognition points that, in interaction with the measurement head, allow the handheld device to recognise the dimensions of the present measuring chamber, and set up the measurement parameters (such as illumination time, light sensitivity). In its simplest form, this dimension-depending recognition points could consist of contact elements distributed across the measurement head of the handheld device, and dependable on the dimensions of the measurement chamber will be unique in their interaction with the contact elements present on the exchangeable measuring chamber.

Another important factor is the miniaturisation of the system to result in a 'handheld' measuring instrument that can be used very flexible in in vivo labs. With this, the user friendliness will in particular be the determining factor for the outer measurements of the device, and there are no special restrictions on the form and dimensions. In practice, one will strive to keep the weight of the handheld device below 500 g.

Speed of the Acquisition

The speed of the acquisition is a determining parameter for the selection of the recording system. After all, one wants to measure the tumour as quickly as possible, even though the mice are immobilised in the hand of the researcher. It still concerns live and awake animals and the total immobilisation during the measurement is not possible. All of this makes the speed of the acquisition a determining factor for the quality of the image recording, and without good image recording, it is also impossible to perform reliable analysis afterwards. The setup based on 3D stereovision with two cameras offers a few important benefits in relation to, for example, existing industrial line scanners. With the intended setup, 1 or a few image recordings are sufficient, and depending on the resolution, the image recording can happen within a few milliseconds. Multiple recordings must be made with a line scanner. Even with a rapid scanner (80 fps) this takes more than a second. During this time, the object should not move, which cannot be guaranteed.

Thus, in a further embodiment of this invention, the measurement system is characterised in the fact that the speed of the image recording is less than $\frac{1}{10}$ s and the images are processed within 10 s.

Description of the System Structure

Figure 3:
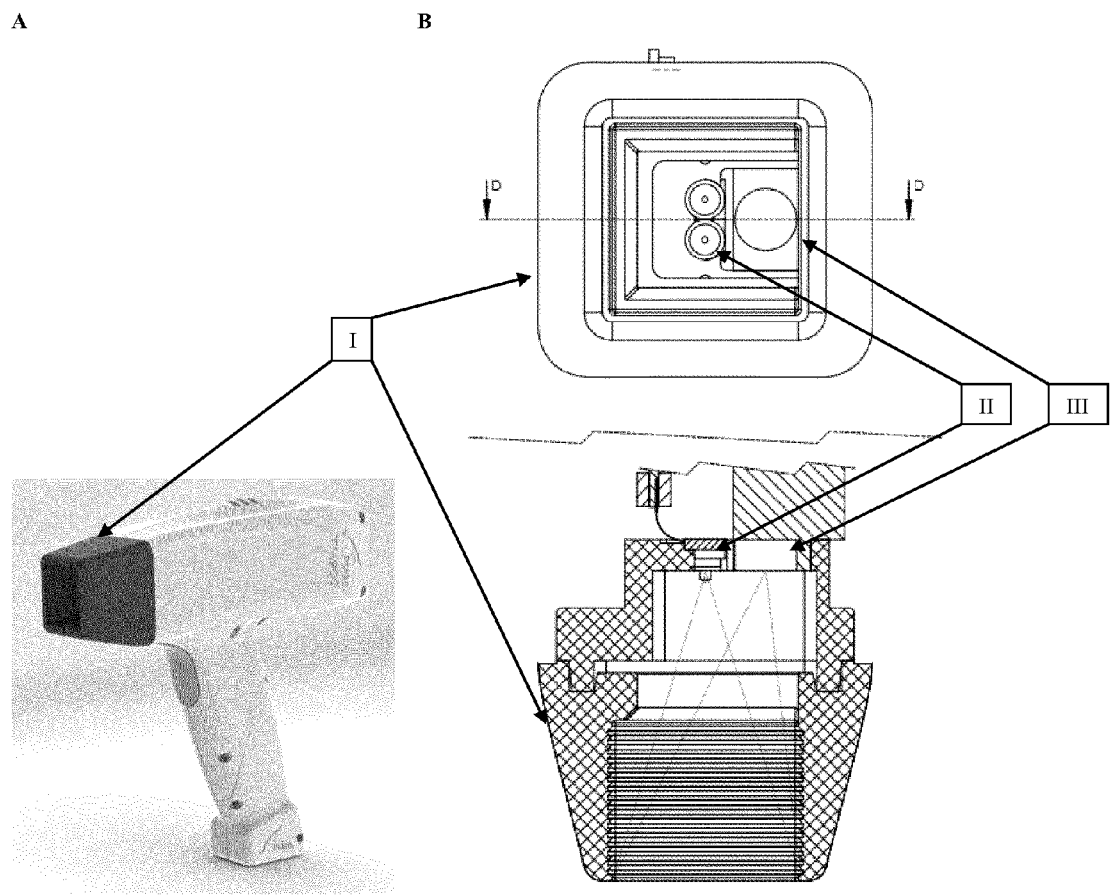
FIG. 3 Side view of the measuring device (A) and technical drawing with the most important components (B).

The structure of the 3D measurement device based on 3D stereovision is compiled based on the previous specifications (see FIG. 3). Everything is built around a handheld device that contains a measurement chamber to measure an object, and can in particular be positioned around the tumour (I). With this device, we use 3 different measurement chambers that are easily exchangeable with dimensions of 30×30×50 mm, 22.5×22.5×50 mm and 15×15×50 mm (L×B×H). At the top of the measurement chamber, and as part of the measurement head of the handheld device, you will find a double camera setup (i.e. the sensors) for stereo-vision (II), preferably small cheap cameras that can be used in SmartPhones, laptops, toys and even gadgets. Custom lenses can also be used to obtain sharp images at a distance of 50 mm and sufficient depth of field. Next to the cameras and as part of the measurement head of the handheld device, you will also find a custom projection system (i.e. the measurement source) for projecting recognisable measure points (for example a structured noise pattern) (III) on to the targeted object. This helps to improve the accuracy of the stereo matching algorithm and for positioning the measuring chamber physically on the target. The projected pattern is preferably a noise pattern based on Hamming codes and green for optimal quality because of the reflection and absorption spectrum of the skin of the mice. In addition to this, the handheld device also has a processor for data acquisition and optionally preliminary data processing. The processor also handles the user interface, consisting of one or more input devices (in particular a pushbutton included in the handle of the handheld device) and one or multiple output devices (in particular one or more light-, image and/or noise signals) to inform the user about the status of the handheld (measuring) device, such as power status, connection/communication status with the base station, data acquisition status, memory status, and such.

In order to record images via built-in cameras, the processor is activated to data acquisition after activation of the push button in the handle of the handheld device. The images are recorded by the processor and saved in the installed RAM memory. These raw images then undergo an optional and first data processing (such as the rectification of the images, tagging the images, stereo calculation, visual control of the image) and are sent to a base station, wireless or in any other way. Standard modules are preferably used. One of the objectives of this invention is then also to offer a measuring system where the handheld device has —a processor module; —a user interface; —power supply; and a data communication interface. In a first embodiment, and in order to perform the previous measuring method, the processor module in the handheld device will contain application code for the user interface; the image recording, the projection, the power supply and the communication interface.

The base station (see FIG. 4) is based on a standard panel-pc. The panel-pc has the required software to further process images from the handheld device into the volume of the measured object. For this purpose, stereo images are converted to a 3D point cloud, the noise is filtered out, and the point cloud is triangulated and the tumour is (semi-) automatically segmented. The stereo-vision algorithms, the structured noise generators and libraries for triangulation are available as Open Source, for example Open CV (Open Source Computer Vision) as part of the ROS application packages ((Konolige, K., Projected texture stereo, Robotics and Automation (ICRA), 2010 IEEE International Conference on; p. 148-155). Possible libraries for triangulation are QHull, Point Cloud, Library (PCL), and such.

The functionality of the base station can be elaborated when needed, with the automatic cage and mouse selection, automatic input of metadata such as, for example, the weight of the mouse and viewing the data history. A connection with a server is recommended for this, so all data is stored in a central database.

Via the management PCs, the experiments, cages and mice can be controlled. The measurements can also be reviewed and reports can be generated.

One of the objectives of this invention is to provide a measurement system that is in particularly suited for the measurement of dimensions, including the volume, of objects of variable forms, including;

A handheld device with a measuring chamber, at least 1 camera and one projector, where the projector projects recognisable marks on the object to be measured and the camera captures one or multiple images of the object to be measured and send this to a base station after a first processing; and A base station with a user interface such as a touch screen, keyboard and/or pointer device, the required software to further process the images from the handheld device into the volume of the measured object, an output device such as a screen, and optionally, a docking- and or loading station for the handheld device to the base station.

In the aforementioned measurement system, the base station could also have additional communication ports such as IEEE 1394, USB, IEEE 1284, Bluetooth, IEEE 802.11n, WiMedia UWB, SCSI and Ethernet to receive input of metadata, such as environment parameters via for example, temperature sensors, the weight of the mouse via an electronic balance, automatic cage selection via, for example RFID chips or barcode scanners; and data history for example available on a remote server, and on the other hand to send the generated data to a remote server and/or management PC's.

In a further embodiment of this invention, the functionality of the handheld device and the base station is integrated in one single device. One of the further objectives of this invention thus is to provide a measurement system that is in particularly suited for the measurement of dimensions, including the volume, of objects of variable shapes, including;

A handheld device as described here, with a measuring chamber, at least one camera, a projector, —a processor module; —a user interface; —power supply; and a data communication interface, where the processor module, in addition to the application code for the user interface; the image recording, the projection, the power supply and the communication interface also has the application code for the image processing.

Optionally, this further embodiment could also have additional communication ports such as IEEE 1394, USB, IEEE 1284, Bluetooth, IEEE 802.11n, WiMedia UWB, SCSI and Ethernet to receive input of metadata, such as environment parameters via for example, temperature sensors; the weight of the mouse via an electronic balance, automatic cage selection via, for example RFID chips or barcode scanners; and data history for example available on a remote server, and on the other hand to send the generated data to a remote server and/or management PC's.

The invention claimed is:

1. A measuring system for 3D measurements of objects in various shapes comprising a handheld device having at least one sensor, at least one measurement source and an exchangeable measuring chamber, wherein said exchangeable measuring chamber is connected to the handheld device; wherein said exchangeable measuring chamber consists of upright faces that fit over the object to be measured on one side and fit on the opposite side on a measuring head of the handheld device; and wherein said exchangeable measuring chamber has dimension-depending recognition points that, in interaction with the measuring head, allow the handheld device to recognize the dimensions of said exchangeable measuring chamber and set up measuring parameters.

2. The measuring system according to claim 1, where the sensor is a camera or an ultrasonic transducer.

3. The measurement system according to claim 1, wherein the measurement source is selected from the group consisting of a projector, a non-ionizing laser, a microwave source and an RF-wave source.

4. The measurement system according to claim 1, wherein the handheld device has two cameras and a projector, and the 3D measurement is based on stereo-vision.

5. The measurement system according to claim 1 wherein the handheld device includes one or more components selected from the group consisting of a processor module, a user interface, a power supply, and a data communication interface.

6. The measuring system according to claim 1 wherein the exchangeable measuring chamber comprises interior dimensions that allow objects to be covered with a variable, non-geometric volume.

7. The measuring system according to claim 1, wherein the exchangeable measurement chamber is about 150 mm in length and width and about 200 mm in height.

8. The measurement system according to claim 1, wherein the exchangeable measuring chamber has grips for connection with the measuring head of the handheld device selected from the group consisting of a threaded connection, bayonet lock, click confirmation, and magnetic adhesion.

9. The measurement system according to claim 1, wherein the exchangeable chamber has a diameter of about 150 mm and a height of about 200 mm.

10. The measurement system according to claim 1, wherein the exchangeable measurement chamber comprises inside walls that include horizontally ribbed panels on one or more internal surfaces thereof.

11. The measurement system according to claim 1, where at least one of the upright faces of the exchangeable measuring chamber allows viewing into the chamber when positioned over the object to be measured.

12. The measuring system according to claim 11, wherein at least one of the upright faces of the exchangeable measuring chamber is either transparent or has been opened.

13. The measurement system according to claim 1, wherein the measurement resolution is about 0.5 to 0.01 mm.

14. The measurement system according to claim 1 wherein the system includes a processor module having application code for the measurement source and the sensor.

15. The measuring system according to claim 14 wherein the system includes a data communication interface connected to a base station with software for image processing of the data generated by the processor module.

16. The measurement system according to claim 15 wherein the software at the base station is capable of calculating 3D points, surface fitting, 3D filtering, recognition and removal of body shape(s), storing and management of measurements, installation and update support, and the generation of a user interface.

17. The measurement system according to claim 1 wherein the system includes a power supply comprising one or more exchangeable loadable batteries.

18. A measuring system according to claim 1 for 3D measurements of objects of variable shapes, wherein the sensor consists of a camera and the measurement source consists of a projector comprising:
   a handheld device with an exchangeable measuring chamber according to claim 1, at least one camera and one projector, where the projector projects recognisable marks on the object to be measured and the camera captures one or multiple images of the object to be measured; and
   a base station with a user interface selected from a touch screen, a keyboard or a pointer device, said base station including software for processing the images from the handheld device to the volume of the measured object, and an output device.

19. A method of measuring subcutaneous cancer tumors in an animal comprising providing the measuring system for 3D measurements of claim 1 and projecting a detectable signal at the surface of the object to be measured, recording the signal as transformed by the object to be measured, and processing the signal to provide a 3D image of the object.

20. The measurement system according to claim 5 wherein the processor module comprises application code for the user interface, the power supply and the data communication interface.

\* \* \* \* \*

UNITED STATES PATENT AND TRADEMARK OFFICE
CERTIFICATE OF CORRECTION

PATENT NO. : 9,445,078 B2
APPLICATION NO. : 14/114569
DATED : September 13, 2016
INVENTOR(S) : Emmanuel Sneyders et al.

It is certified that error appears in the above-identified patent and that said Letters Patent is hereby corrected as shown below:

On the Title Page

Item (75):
"Emmanuel Sneyders, Turnhout (BE);
Jean Marie Stassen, Heverlee (BE);
Hans Nicasy, Turnhout (BE)"
Should read:
--Emmanuel Sneyders, Beerse (BE);
Jean Marie Stassen, Deurne (BE);
Hans Nicasy, Turnhout (BE)--;

In the Specification

Column 1, Line 41:
"The tumour size is the primary focus in most preclinical"
Should read:
--The tumor size is the primary focus in most preclinical--;

Column 1, Line 43:
"tumours are thus crucial for a speedy evaluation of new"
Should read:
--tumors are thus crucial for a speedy evaluation of new--;

Column 1, Lines 46 and 47:
"ponents on subcutaneous or orthotopic tumours is studied. The subcutaneous tumour models with immune deficiency,"
Should read:
--ponents on subcutaneous or orthotopic tumors is studied. The subcutaneous tumor models with immune deficiency,--;

Signed and Sealed this
Fourth Day of December, 2018

Andrei Iancu
*Director of the United States Patent and Trademark Office*

CERTIFICATE OF CORRECTION (continued)
U.S. Pat. No. 9,445,078 B2

Figure 1:
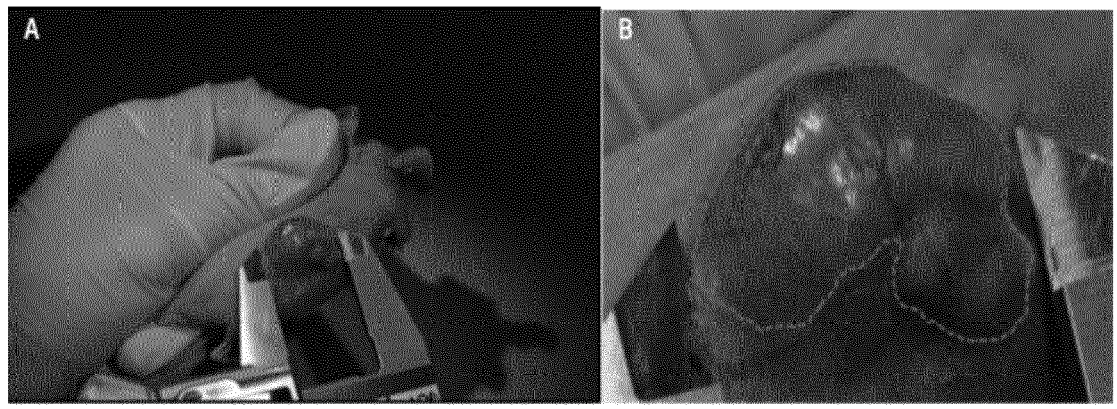
FIG. 1 Subcutaneous tumours are measured with calipers (A). These tumours could have various shapes (B).

Column 1, Line 58:
"term experiments, where the tumour growth is monitored"
Should read:
--term experiments, where the tumor growth is monitored--;

Column 1, Line 65:
"light-based system for scanning subcutaneous tumours in"
Should read:
--light-based system for scanning subcutaneous tumors in--;

Column 2, Line 5:
"For this reason, the subcutaneous tumour growth is often"
Should read:
--For this reason, the subcutaneous tumor growth is often--;

Column 2, Line 9:
"eters and the maximum height. As the tumours grow, the"
Should read:
--eters and the maximum height. As the tumors grow, the--;

Column 2, Line 13:
"tumour size. Not only intensive training and experience are"
Should read:
--tumor size. Not only intensive training and experience are--;

Column 2, Line 20:
"the growth of subcutaneous tumours. With the new measur-"
Should read:
--the growth of subcutaneous tumors. With the new measur- --;

Column 2, Line 37:
"angles, the latter being combined in a D-stereovision algo-"
Should read:
--angles, the latter being combined in a 3D-stereovision algo--;

Column 2, Line 61:
"tumours in laboratory animals as described hereinbefore. In"
Should read:
--tumors in laboratory animals as described hereinbefore. In--;

Column 3, Line 3:
"subcutaneous tumours."
Should read:
--subcutaneous tumors.--;

Column 3, Lines 7 and 8:
"FIG. 1 Subcutaneous tumours are measured with calipers (A). These tumours could have various shapes (B)."
Should read:
--FIG. 1 Subcutaneous tumors are measured with calipers (A). These tumors could have various shapes (B).--;

Column 3, Line 37:
"subcutaneous tumours in various animal models for cancer."
Should read:
--subcutaneous tumors in various animal models for cancer.--;

Column 3, Lines 56 and 57:
"throughput screening of the effect of tumour inhibitors on subcutaneous tumour growth. In the current situation, where"
Should read:
--throughput screening of the effect of tumor inhibitors on subcutaneous tumor growth. In the current situation, where--;

Column 4, Line 5:
"tumours. The parameters that determine this image record-"
Should read:
--tumors. The parameters that determine this image record- --;

Column 4, Line 16:
"measurement source will consists of non-ionizing laser"
Should read:
--measurement source will consist of non-ionizing laser--;

Column 4, Lines 43-44:
"neous tumours in mice. Further, the integration of the device in the research process on "subcutaneous mouse-tumours""
Should read:
--neous tumors in mice. Further, the integration of the device in the research process on "subcutaneous mouse-tumors--;

Column 4, Line 48:
"same tumour measured by the various operators, decreases"
Should read:
--same tumor measured by the various operators, decreases--;

Column 5, Line 39:
"points can be found on both cameras recordings. Via these"
Should read:
--points can be found on both camera recordings. Via these--;

Column 5, Line 56:
"particular in the measurement of subcutaneous tumours in mice, one wants to measure the tumour as quick as possible,"
Should read:
--particular in the measurement of subcutaneous tumors in mice, one wants to measure the tumor as quick as possible,--;

Column 6, Lines 8 and 9:
"subcutaneous tumours, the typical shapes and dimensions of these tumours will be taken into consideration for determin-"
Should read:
--subcutaneous tumors, the typical shapes and dimensions of these tumors will be taken into consideration for determin- --;

Column 6, Line 65:
"mm and a height of approximately mm; and in its smallest"
Should read:
--mm and a height of approximately 50 mm; and in its smallest--;

Column 7, Line 24:
"to measure the tumour as quickly as possible, even though"
Should read:
--to measure the tumor as quickly as possible, even though--;

Column 7, Line 49:
"and can in particular be positioned around the tumour (I)."
Should read:
--and can in particular be positioned around the tumor (I).--;

Column 8, Line 36:
"the point cloud is triangulated and the tumour is (semi-)"
Should read:
--the point cloud is triangulated and the tumor is (semi-)--; and Column 8, Line 55:
"measurement system that is in particularly suited for the"
Should read:
--measurement system that is particularly suited for the--.